United States Patent

Woloch

[11] Patent Number: 5,845,358
[45] Date of Patent: Dec. 8, 1998

[54] COMBINATION TOOTHBRUSH AND TONGUE SCRAPER

[76] Inventor: Heather N. Woloch, 1151 Powder Spring Rd., Sevierville, Tenn. 37876

[21] Appl. No.: 1,962

[22] Filed: Jan. 2, 1998

[51] Int. Cl.[6] .................................................... A47L 13/12
[52] U.S. Cl. ............................ 15/111; 15/167.1; 606/161; D4/108
[58] Field of Search .................................. 15/111, 167.1, 15/110; 606/161; D4/108, 118

[56] References Cited

U.S. PATENT DOCUMENTS

| | | | |
|---|---|---|---|
| 1,495,675 | 5/1924 | Colt | 15/111 |
| 5,005,246 | 4/1991 | Yen-Hui | 15/111 |
| 5,569,278 | 10/1996 | Persad | 15/111 |
| 5,709,004 | 1/1998 | Paduano et al. | 15/111 |

FOREIGN PATENT DOCUMENTS

| | | | |
|---|---|---|---|
| 734846 | 10/1932 | France | 606/161 |
| 2027347 | 2/1980 | United Kingdom | 606/161 |

*Primary Examiner*—Gary K. Graham

[57] ABSTRACT

A toothbrush provided with a flexible tongue scraper movably received in separable halves of a hollow toothbrush handle. Separation of the toothbrush handle reveals the tongue scraper. The tongue scraper has enlarged ends which are retained in reduced passages in the handle halves.

1 Claim, 3 Drawing Sheets

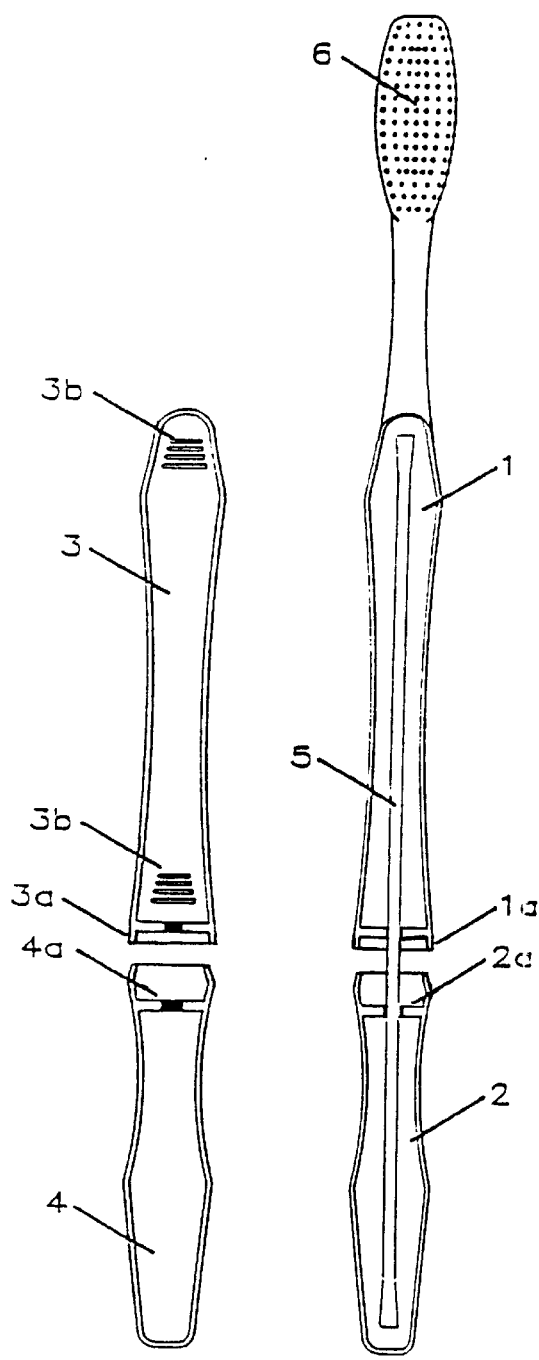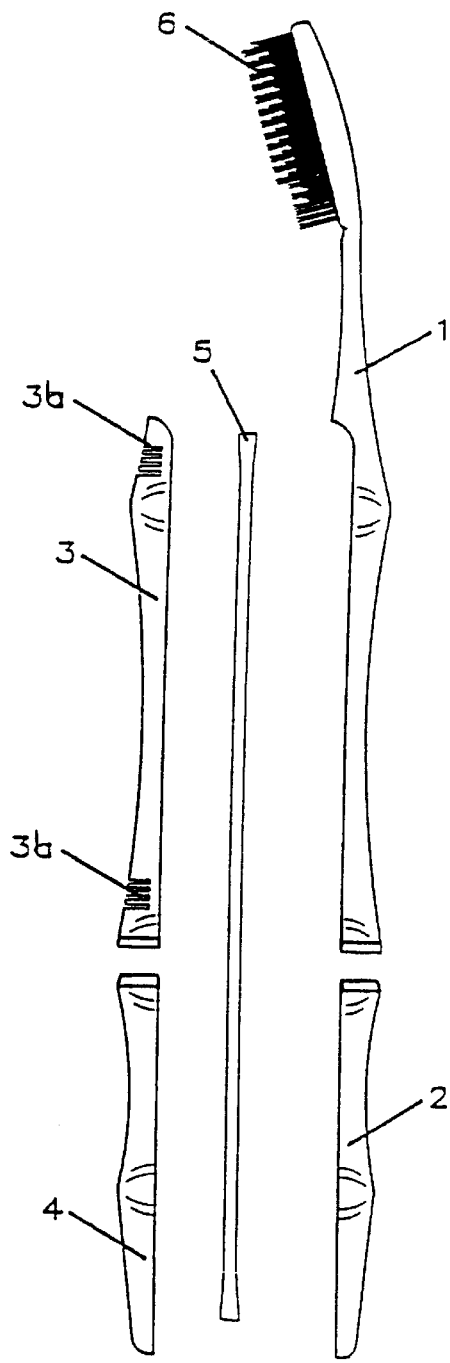
Fig. 5
Fig. 6

COMBINATION TOOTHBRUSH AND TONGUE SCRAPER

BACKGROUND FIELD OF INVENTION

This invention relates to the combination toothbrush and tongue scrapers, specifically to a superior oral hygiene tool which effectively combines a tongue scraper with an ordinary toothbrush.

BACKGROUND DESCRIPTION OF PRIOR ART

Currently there are five patents for combination toothbrush and tongue scrapers, U.S. Des. Pat. No. 295,343 to Regalado, Apr. 26, 1983. U.S. Des. Pat. No. 246,878 to kitzis, Jan. 10, 1978. U.S. Pat. No. 4,488,327 to Snider, Dec. 18 1984. U.S. Des. Pat. No 295,695 to Gelanri, May 17 988. U.S. Pat. No. 5,530,981 to Wen-sqn Chen Jul. 2 1996. None of these products have been successful die to the impracticality of their designs. Due to the rigid and builky design seen in all of the above mentioned patents the user would not be able to effectively scrape the entire tongues surface due to the space limitations in of the mouth.

The design of my combination toothbrush and tongue scraper solves the problem of space limitations in the mouth due to the small size of the tongue scraper. With my smaller scraper the user will be able to scraper the entire tongue easily and will be less likely to trigger the gag reflex. Also the toothbrush broken in half will serve as handles for the tongue scraper. This feature gives the user greater control of the tongue scraper.

objects and advantags

Accordingly, besides the objects and advantages of the small and pliable tongue scraper which is housed inside a toothbrush that acts as handles for the tongue scraper, several objects and ges of this invention are:

(a) to provide a small enough tongue scraper to effectively remove plaque build-up on the tongue comfortably.

(b) to provide a convenient, all in one oral hygiene tool.

further objects and advantages are to provide a superior oral hygiene tool which will effectively remove plaque deposits from all oral surfaces.

BRIEF DESCRIPTION OF THE DRAWINGS

In the drawings, closely related figures have the same number but different alphabetical suffixes.

FIG. 5 is an exploded view of the toothbrush.

FIG. 6 also shows an exploded view.

Figure 1:
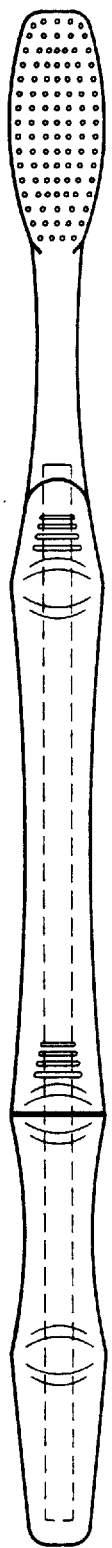
FIG. 1 shows the top view of the toothbrush, the broken line represents the tongue scraper inside.
Figure 2:
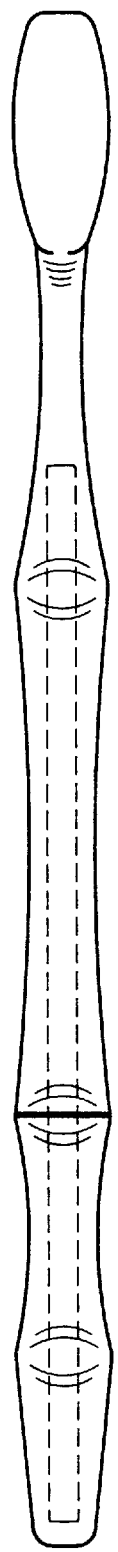
FIG. 2 shoes the back view of the toothbrush.

REFERENCE NUMERALS IN DRAWINGS 1 back piece of toothbrush with head
2 back piece of the bottom of toothbrush
3 front of the top half of toothbrush
4 front of the bottom half of toothbrush
5 tongue scraper with thickened ends
6 head of the toothbrush
2a and 4a illustrates the flute which the tongue scraper slides through, also the frustrum which pushes into the bougie of the top of toothbrush
1a and 3a illustrates the bougie of top of toothbrush where the frustrum of bottom half of toothbrush will be pushed into
3b vents

SUMMARY

Figures 3, 4:
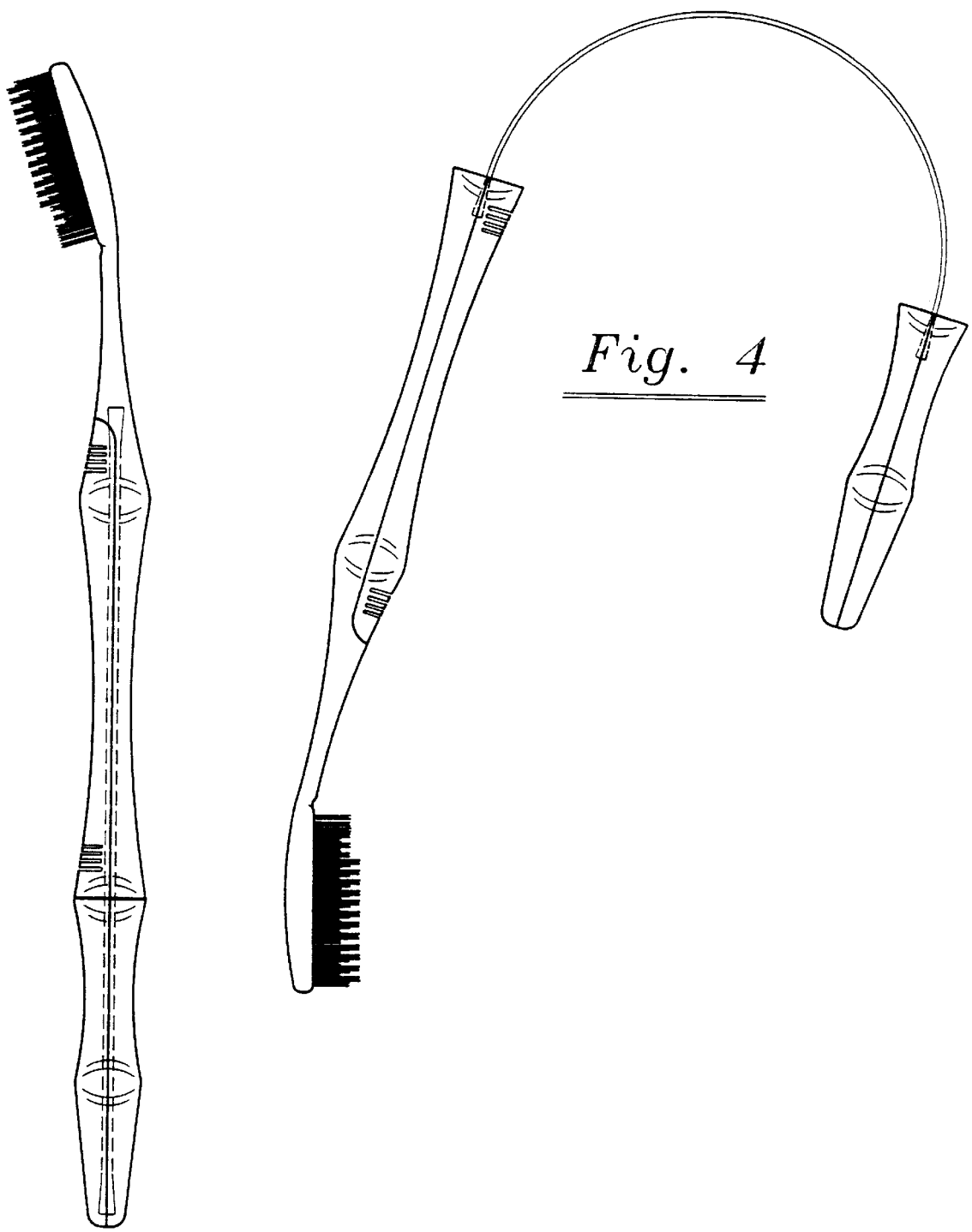
FIG. 3 shows the profile of the toothbrush.
FIG. 4 Demonstrates how the tongue scraper is exposed for use, also how the toothbrush breaks down to serve as handles for the tongue scraper.

The typical embodiment of the toothbrush and tongue scraper combination is illustrated in FIG. 4. When the toothbrush is pulled apart the tongue scraper is exposed and remains connected to the toothbrush, the two separated pieces of the toothbrush serve as handles for the tongue scraper. The user may also remove the tongue scraper from the toothbrush and use separately if desired. This invention is the most comprehensive oral hygiene to date due to its all in one design. It is designed to remove plaque from the user entire mouth, especially the plaque that cause bad breath at the back of the tongue.

DESCRIPTION OF INVENTION

FIG. 4 shows an overall view of the toothbrush and tongue scraper of the invention. This illustrates the tongue scraper in its working position. The tongue scraper 5 is an elongated flexible member with enlarged ends. The enlarged ends are movably received in first and second halves of the brush handle which can be separated when the scraper is desired to be used. The enlarged ends are retained in the respective halves by reduced passages through which the ends cannot pass. FIGS. 5 and 6 are exploded views of the invention. In these views numbers 1 and 2 are the back of the toothbrush and numbers 3 and 4 are the front. The toothbrush will be injection molded, possibly with a polypropylene or a comparable material. The tongue scraper is number 5 and can be made with a number of different flexible plastics, also to be injection molded. Numbers 2a and 4a shows the flute that the tongue scraper will slide through inside the toothbrush. Numbers 1a and 3a shows the bougie that the bottom half of the toothbrush will be pushed into for a tight fit. This connection is comparable to the way that you push a top onto an ink pen for a tight fit.

Operation-Main Embodiment

In the use of the combination toothbrush and tongue scraper the user will brush their teeth in the usual manner. The user will then pull the toothbrush apart to expose the tongue scraper as illustrated in FIG. 4. In this position the two separated halves of the toothbrush serve as handles for the tongue scraper. The user will then scrape the plaque deposits from the tongue that cause bad breath, leaving the user with a cleaner mouth than ever before. The user will then rinse the tongue scraper and push the toothbrush back together and store like any other toothbrush. Thus having described the preferred embodiment of the invention, it should be understood that many structural modifications and adaptations may be resorted to without departing from the spirit of this invention.

Description-Alternative Embodiments

There may be many structural modifications and adaptations that could be resorted to without departing from the spirit of this invention.

Conclusion, Ramifications, and Scope

Thus the reader will see that the combination toothbrush and tongue scraper is a useful device that can be used by persons of almost any age.

The combination toothbrush and tongue scraper combines two of the most oral hygiene products. The toothbrush which will be used in the usual manor after which the toothbrush will be pulled apart to expose the tongues scraper inside. The two halves of the toothbrush will serve as handles for the tongue scraper as shown in FIG.4. In this position the tongue scraper will be placed at the back of the tongue with the mouth partially closed so not to trigger the gag reflex. With other tongue scrapers the mouth is required to be fully open which will trigger the gag reflex when the scraper is placed at the back of the tongue. With the design of this tongue scraper being so thin it allows the user to scrape their tongue with their mouth almost fully closed and in this position you are less likely to trigger the gag reflex.

Although the description above contains many specificities, these should not be construed as limiting the scope of the invention but as merely providing illustrations of some of the presently preferred embodiments of is invention. For example, the toothbrush may be longer than an average toothbrush, different shapes other than cylindrical or rectangular, the tongue scraper is connected to the hollow of the toothbrush but it may be removed, etc.

I claim:

1. A toothbrush and tongue scraper device, said device comprising:

an elongated hollow handle defining first and second ends, a bristled brush head secured to said first end of said handle, said handle being separable intermediate said ends into first and second elongated halves, each elongated half being hollow to define a channel therein, each half having at said separation a reduced passage leading to a respective channel, an elongated strip of flexible material having first and second opposed enlarged ends, said strip received in said halves and passing through said reduced passages such that separation of said handle causes said strip to become exposed, wherein said enlarged ends cannot pass through said reduced passages.

* * * * *